United States Patent
Friedman et al.

(10) Patent No.: US 6,774,800 B2
(45) Date of Patent: Aug. 10, 2004

(54) PATIENT INCONTINENCE MONITORING APPARATUS AND METHOD OF USE THEREOF

(75) Inventors: Mark B. Friedman, Pittsburgh, PA (US); Randall W. Casciola, Pittsburgh, PA (US)

(73) Assignee: AugmenTech, Inc., Pittsburgh, PA (US)

( * ) Notice: Subject to any disclaimer, the term of this patent is extended or adjusted under 35 U.S.C. 154(b) by 0 days.

(21) Appl. No.: 10/113,164

(22) Filed: Apr. 1, 2002

(65) Prior Publication Data

US 2002/0145525 A1 Oct. 10, 2002

Related U.S. Application Data

(60) Provisional application No. 60/280,274, filed on Mar. 30, 2001.

(51) Int. Cl.$^7$ .................. G08B 23/00; G08B 13/14; G08B 21/00; A61F 13/15
(52) U.S. Cl. .................. 340/573.5; 340/572.5; 340/604; 604/361
(58) Field of Search .................. 340/604, 572.4, 340/572.5, 573.5; 604/361

(56) References Cited

U.S. PATENT DOCUMENTS

| | | | | |
|---|---|---|---|---|
| 3,759,246 A | * | 9/1973 | Flack et al. ............... 600/573 |
| 3,810,147 A | | 5/1974 | Lichblau ................... 340/280 |
| 3,967,161 A | * | 6/1976 | Lichtblau .................. 361/765 |
| 5,317,330 A | * | 5/1994 | Everett et al. ............. 343/867 |
| 5,463,377 A | * | 10/1995 | Kronberg .................. 340/605 |
| 5,570,082 A | * | 10/1996 | Mahgerefteh et al. ...... 340/604 |
| 5,904,671 A | * | 5/1999 | Navot et al. .............. 604/361 |
| 5,941,836 A | | 8/1999 | Friedman ................... 600/595 |
| 5,963,134 A | | 10/1999 | Bowers et al. ............ 340/572.1 |
| 6,025,783 A | * | 2/2000 | Steffens, Jr. .............. 340/644 |
| 6,043,746 A | | 3/2000 | Sorrells ................... 340/572.7 |
| 6,182,352 B1 | * | 2/2001 | Deschenes et al. ........ 29/602.1 |
| 6,246,330 B1 | * | 6/2001 | Nielsen ..................... 604/361 |
| 6,249,229 B1 | | 6/2001 | Eckstein et al. .......... 340/572.4 |
| 6,294,997 B1 | * | 9/2001 | Paratore et al. .......... 340/572.1 |
| 6,384,728 B1 | * | 5/2002 | Kanor et al. ............. 340/573.1 |
| 6,407,308 B1 | * | 6/2002 | Roe et al. ................. 604/361 |
| 6,583,722 B2 | * | 6/2003 | Jeutter et al. ............ 340/573.1 |

OTHER PUBLICATIONS

United States Patent Application Publication US 2001/0040507 A1; Nov. 15, 2001; Eckstein et al.

* cited by examiner

Primary Examiner—Jeffery Horsass
Assistant Examiner—Anne V. Lai
(74) Attorney, Agent, or Firm—Webb Ziesenheim Logsdon Orkin & Hanson, P.C.

(57) ABSTRACT

A patient fluid discharge monitoring method and apparatus includes at least one article configured to be worn by a patient, the article having absorbent material and a RF tag received adjacent the absorbent material. The RF tag is excited with an excitation signal and the response of the RF tag to the excitation signal is detected. The detected response of the RF tag is compared to a predetermined response. The RF tag has a first detected response when the absorbent material has no fluid therein and a second detected response when the absorbent material has fluid therein.

29 Claims, 9 Drawing Sheets

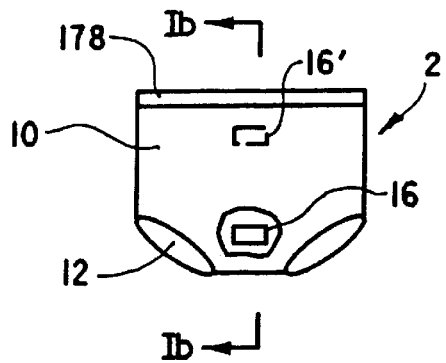
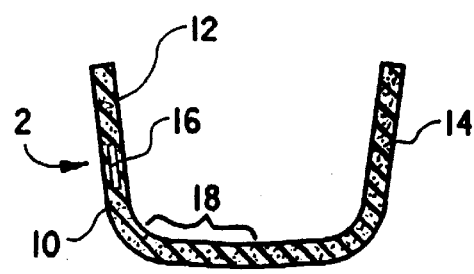
FIG. 1a     FIG. 1b
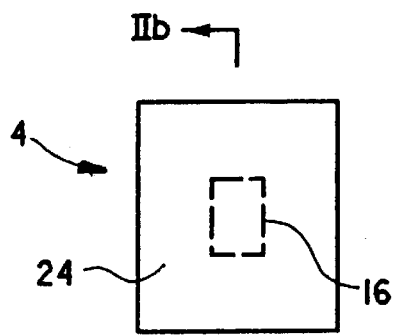
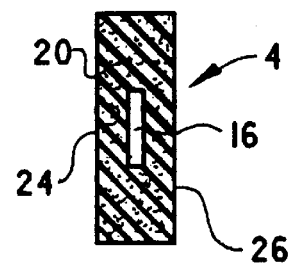
FIG. 2a     FIG. 2b
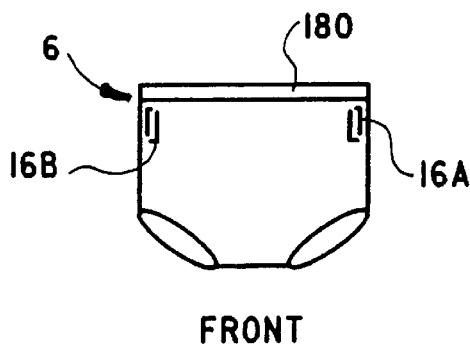
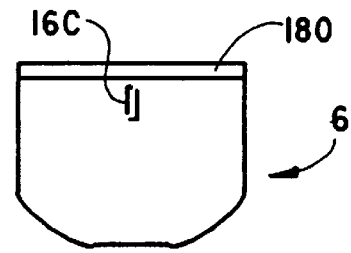
FRONT     BACK
FIG. 3a     FIG. 3b

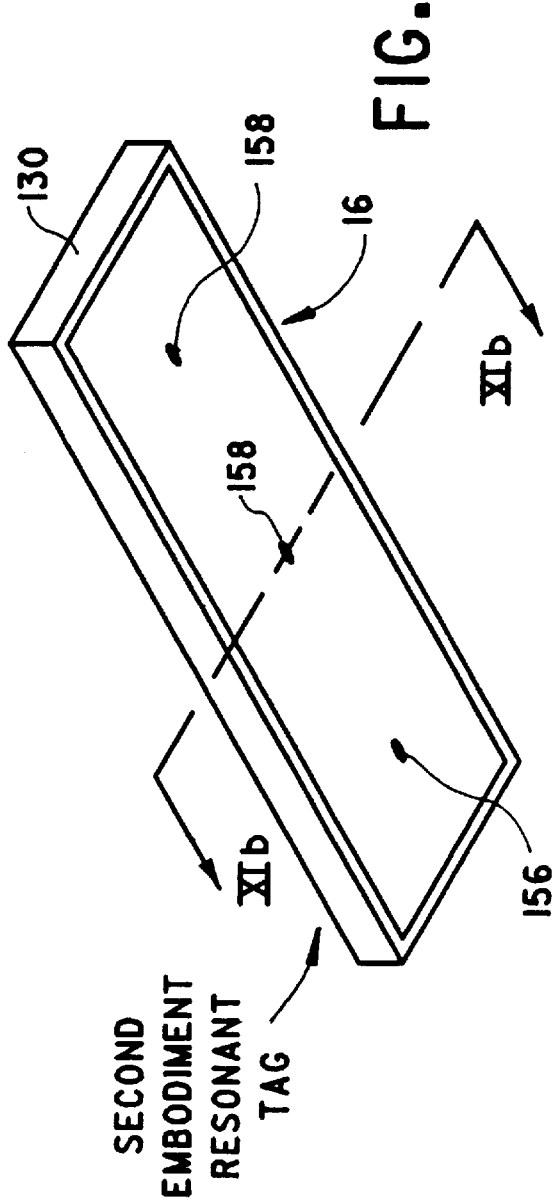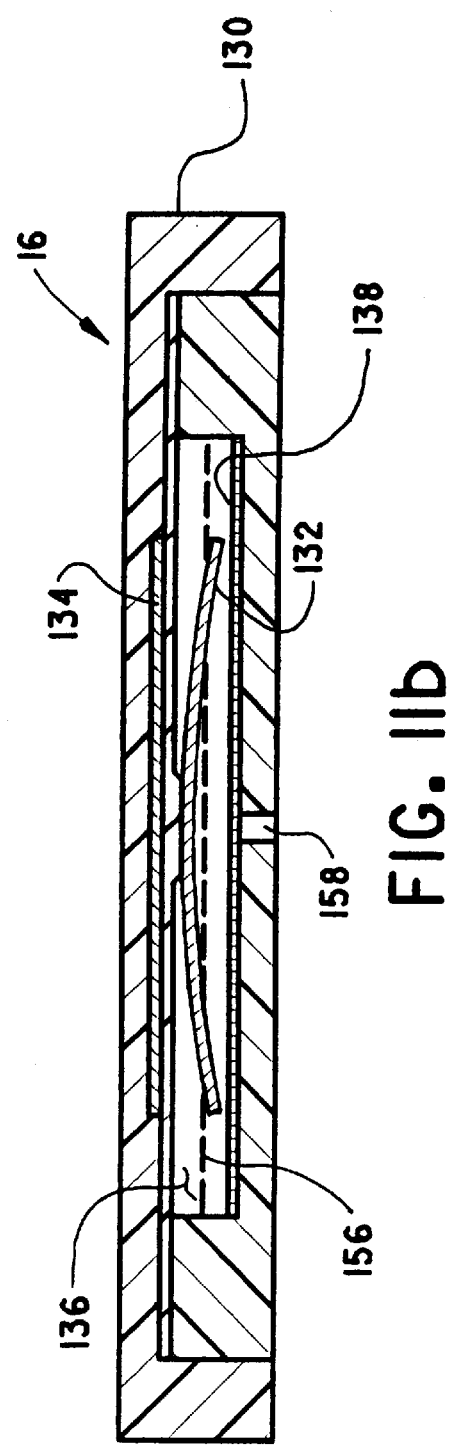

PATIENT INCONTINENCE MONITORING APPARATUS AND METHOD OF USE THEREOF

CROSS REFERENCE TO RELATED APPLICATION

This application claims priority from U.S. Provisional Patent Application Serial No. 60/280,274, filed Mar. 30, 2001.

BACKGROUND OF THE INVENTION

1. Field of the Invention

The present invention relates to incontinence monitoring and/or position monitoring of patients.

2. Description of Related Art

Incontinence is universal among the very young and increasingly common among the very old. Incontinence may also be a consequence of surgical procedures or neurological impairments. There is a need to determine when an absorbent product, e.g., a diaper or bed pad, for a patient who is incontinent is wet, without disturbing the patient.

A wide variety of means have been devised to detect when a diaper is wet without removing the diaper. These include visual indicators and electronic wetness detection systems. Visible indicators for disposable diapers typically are chemicals within the deep layers of the diaper, adjacent to a translucent moisture impermeable outer layer, that change color when wet. For a caregiver to see that the diaper is wet and needs to be changed, the indicator region of the diaper must be visible. This requires undressing the wearer of the diaper when the user is dressed, and pulling back blankets, sheets and bed clothes when the wearer is in bed. It also may require rolling a wearer over to view the rear of the diaper if the wearer is asleep on their back. The process of obtaining a view of chemical wetness indictors is clearly disruptive of the wearers activities. It may be particularly disruptive when checking for wetness awakes a sleeper whether or not their diaper is actually wet and in need of changing. The chief virtue of visible wetness indicators is that they are inexpensive to produce.

Various electronic diaper wetness detection indication systems have been developed specifically to provide remote sensing of when a diaper needs to be changed. These typically involve at least two components attached to the diaper. Systems dependent on radio transmitters also require a remote radio receiver. Electronic wetness detection systems usually have an inexpensive disposable sensor within the diaper and a reusable alarm or transmitter attached to the outside of the diaper that is connected to the wetness sensor within. Typically, the sensing element includes two or more conducting elements separated by a wetable membrane that insulates between the conductors when dry and conducts electricity or otherwise changes impedance between the sensor when wet with urine or other electrolyte solutions. The electrical power that activates the external signaling circuit may be sourced from a battery in the attached electronics package or by galvanic reaction between metallic electrodes in the diaper.

For audio alarms, the detachable reusable electronic package produces an audible signal to alert the caregiver when urine is sensed within the diaper. For radio frequency (RF) alerting systems, a radio transmission is made by the reusable external transmitter when urine is sensed within the diaper. This RF transmission is received by a remote device that is configured to alert a caregiver that the diaper is wet.

Audible electronic systems have the disadvantage of requiring the caregiver to be within hearing range at the time the audible alert is generated. Furthermore, sound generated can be disruptive of ongoing activities, such as sleep or social interaction, particularly for incontinent adults. Radio alerting systems can be more private in signaling the need to change a wet diaper or incontinence bed pad.

While the electronic systems described above have the advantage of not requiring a caregiver to physically disturb the wearer of the diaper in order to determine if the diaper is wet, the reusable electronics package attached to the diaper may be uncomfortably large and must be recovered after each diaper change for reattachment to a fresh diaper. The need to recover and reuse a relatively expensive electronics package attached to a soiled diaper every time the diaper is changed is onerous, especially when the diaper is soiled with feces. Experience shows that the detachable electronics packages are often misplaced or lost in institutional settings when diapers are removed because wearers are being bathed or changed or having a medical procedure.

One type of prior art electronic wetness sensor for incontinence products includes two or more sensing elements separated by an insulating region, attached to the electronic sensing circuit. Usually, these sense wetness by the increased conductance between two electrodes, but changing capacitance has also been used to detect wetness. A problem with these types of prior art incontinence detecting systems is that they require the attachment of a powered audible or radio-signaling device to the diaper and that they require sensing electrodes to function.

Another prior art electronic wetness sensor for incontinence products is disclosed in U.S. Pat. No. 5,570,082 to Mahgerefteh et al. This wetness sensor includes a circuit having two spaced sensing elements connected in series with an antenna and a nonlinear element, e.g., a semiconductor diode. In the absence of discharged urine, the circuit is not responsive to a magnetic excitation signal due to the lack of conduction between the two sensing elements. However, when discharged urine forms a conductive path between the two sensing elements, the circuit is enabled to respond to the magnetic excitation by imposing detectable harmonics thereon. A problem with this type of prior art incontinence detecting system is its lack of a response when discharged urine does not form a conducting path between the two sensing electrodes.

It is, therefore, an object of the present invention to overcome the above problems and others by providing a system and method of use thereof for remotely detecting when a diaper is wet or when it is not wet without the need to attach a powered signaling device to the diaper. It is an object of the present invention to provide a system and method of use thereof for remotely detecting the position of a patient. Still further objects will become apparent to those of ordinary skill in the art upon reading and understanding the following detailed description.

SUMMARY OF THE INVENTION

Accordingly, we have invented a patient fluid discharge monitoring system that includes a liquid absorbent material configured to be positioned to receive fluid discharged from at least one of urine discharge orifice and a fecal discharge orifice of a patient. A first RF tag is positioned in contact with or in spaced relation with the liquid absorbent material. The first RF tag is responsive to a wireless excitation signal in the absence of discharged fluid in the liquid absorbent material and responsive to the excitation signal in the presence of discharged fluid in the liquid absorbent material for causing at least one of (i) a unique change in the excitation signal and (ii) a change in a unique wireless response signal output by the first RF tag in response to the wireless excitation signal.

The system can include means for transmitting the excitation signal and means for detecting any change in the excitation signal and/or the response signal. The first RF tag can include an inductor coupled in parallel with a capacitive storage element, a magnetostrictive element biased in a magnetic field of a magnet, or an antenna coupled to an integrated circuit (RFID tag) that is responsive to the excitation signal received by the antenna for causing a unique change in the excitation signal or the response signal.

A dry electrolyte can be included in the liquid absorbent material and/or on the first RF tag. When discharged fluid combines with the dry electrolyte, the combination detunes the first RF tag from its resonant frequency and/or shields the first RF tag from the excitation signal.

The absorbent material can be received in a diaper having the absorbent material and the first RF tag received between an inner lining and an outer lining that is at least in part fluid permeable, or in a pad having the absorbent material and the first RF tag received in a casing that is at least in part fluid permeable.

The system can further include a transceiver for supplying the excitation signal to the first RF tag and for detecting the change in the excitation signal and/or the response signal. A detector can process the change detected by the transceiver and generate a signal as a function of the detected change.

A second RF tag can also be positioned in contact with or in spaced relation with the liquid absorbent material. The second RF tag is responsive to a wireless excitation signal in the absence of discharged fluid in the liquid absorbent material and responsive to the excitation signal in the presence of discharged fluid in the liquid absorbent material for causing at least one of (i) a unique change in the excitation signal and (ii) a change in a unique wireless response signal output by the second RF tag in response to the excitation signal.

The second RF tag can be spaced from the first RF tag whereupon discharged fluid received in the absorbent material first causes the first RF tag to respond and cause any change in the excitation signal and/or its response signal and then causes the second RF tag to respond and cause any change in the excitation signal and/or its response signal. The first and second RF tags can also be formed on a common flexible substrate. In order to distinguish the first RF tag from the second RF tag, the unique change in the excitation signal caused by the first RF tag is different than the unique change in the excitation signal caused by the second RF tag. In response to flexing of the substrate, the unique changes in the excitation signal caused by the first and second RF tags change together whereupon the difference between the changes in the excitation signal remain substantially the same.

We have also invented a patient fluid discharge monitoring system that includes an article configured to be worn next to the skin of a patient. The article includes an absorbent material for absorbing fluid discharged by the patient. An RF tag is positioned adjacent the absorbent material. The absorbent material and the RF tag are arranged whereupon in the absence of fluid in the absorbent material the RF tag has a first detected response to a wireless excitation signal and in the presence of fluid in the absorbent material the RF tag has a second detected response to the excitation signal. The second detected response can be a null.

The system further includes means for generating the excitation signal, means for detecting each response of the RF tag to the excitation signal and means for generating a signal as a function of at least one response of the RF tag.

A dry electrolyte can contact or cover at least part of the RF tag. In response to fluid combining with the dry electrolyte, the combination attenuates the excitation signal received by the RF tag and/or detunes a resonant frequency of the RF tag.

The article can be a diaper or a pad, such as an incontinence pad or bandage, having a cover or lining that is at least in part fluid permeable.

The system can include another RF tag positioned adjacent the absorbent material. The absorbent material and the other RF tag are arranged whereupon in the absence of fluid in the absorbent material the other RF tag has a first detected response to the excitation signal and in the presence of fluid in the absorbent material the other RF tags second detected response to the excitation signal. Alternatively, the other RF tag can be positioned in the article and isolated from the absorbent material whereupon the other RF tags one detected response to the excitation signal regardless of the presence or absence of discharged fluid in the absorbent material.

One RF tag can be positioned in the article to provide a first delay between the first and second detected responses thereof when the article receives discharged fluid in the form of urine and another RF tag positioned in the article to provide a second delay between the first and second detected responses thereof when the article receives discharged fluid in the form of moist fecal discharge, wherein the second delay is shorter than the first delay.

Lastly, we have invented a method of monitoring patient fluid discharge. The method includes providing at least one article configured to be worn by a patient. The article includes absorbent material and an RF tag received adjacent the absorbent material. The RF tag is excited with an excitation signal and the response of the RF tag to the excitation signal is detected. The detected response of the RF tag is compared to a reference response wherein the RF tag has a first detected response when the absorbent material has no fluid therein and a second detected response when the absorbent material has fluid therein. The second detected response can be a null.

The reference response and the first detected response can be substantially the same, however, the reference response and the second detected response are different. The method can further include generating an alarm in response to detecting the difference between the reference response and the second detected response.

The second detected response of the RF tag can include a lower amplitude than the first response and/or a different frequency than the first response.

A plurality of RF tags can be distributed throughout the article. The second detected response of each RF tag can occur in response to the absorbent material adjacent the RF tag having fluid therein. The RF tags can be arranged in the article whereupon fluid received in the absorbent material arrives adjacent each RF tag at a different time.

BRIEF DESCRIPTION OF THE DRAWINGS

FIG. 1a is a front view of a disposable diaper including a RF tag therein;

FIG. 1b is a section taken along lines Ib—Ib in FIG. 1a;

FIG. 2(a) is a top view of a pad including an RF tag;

FIG. 2b is a section taken along lines IIb—IIb in FIG. 2a;

FIGS. 3a and 3b are front and back views of an undergarment including RF tags affixed thereto;

FIG. 11a is a perspective view of a second embodiment RF tag;

FIG. 11b is a section taken along lines XIb—XIb in FIG. 11a;

DETAILED DESCRIPTION OF THE INVENTION

Figure 4A:
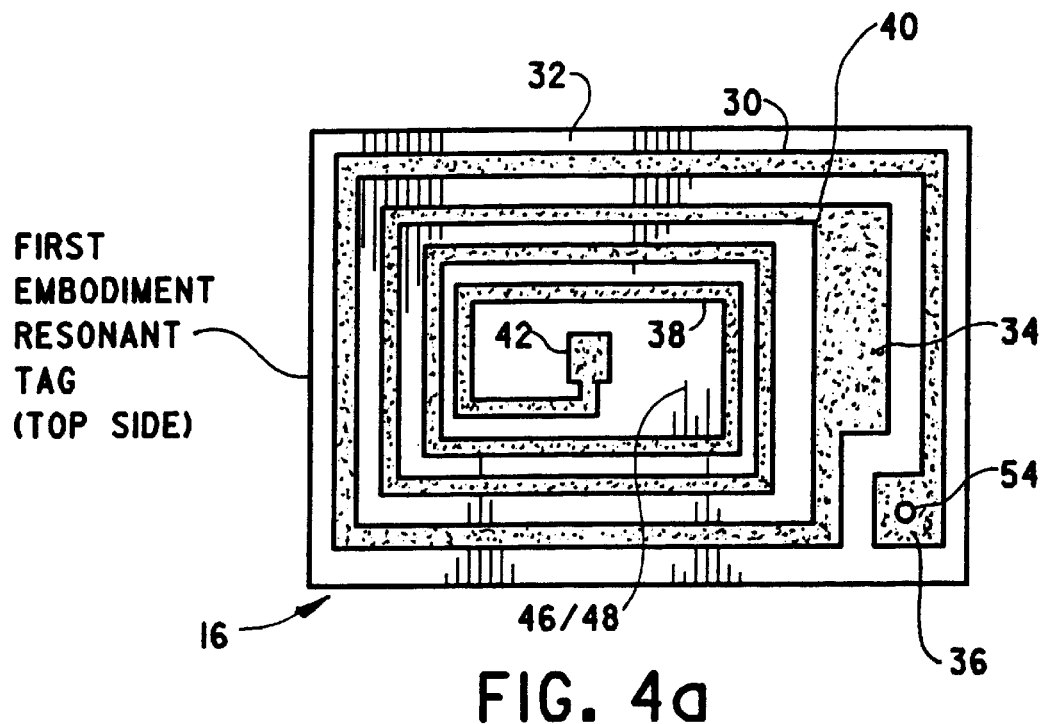
FIGS. 4a and 4b are top and bottom views of a first embodiment RF tag.

The present invention will be described with reference to the accompanying figures. where like reference numbers correspond to like elements.

The present invention is directed to remote patient incontinence monitoring and/or remote patient position monitoring. In connection with patient incontinence monitoring, an article configured to receive fluid discharged from a patient is provided. The article can be a disposable diaper 2, shown in FIGS. 1a and 1b, and/or a disposable pad 4, shown in FIGS. 2a and 2b, or any other article that is suitable for receiving fluid discharged by a patient. In connection with patient positioning monitoring, the article can be diaper 2 or underwear or undergarment 6, as shown in FIGS. 3a and 3b, or any other article that can be worn by a patient without substantial movement of the article with respect to the patient. In the following discussion, use of the invention for patient incontinence monitoring will be first described followed by use of the invention for patient position monitoring.

With reference to FIGS. 1a and 1b, disposable diaper 2 includes an outer, fluid impermeable cover 10, an inner lining 12 and liquid absorbent material 14 therebetween. An RF tag 16 is received between outer cover 10 and inner lining 12 with one or more circuit elements (described hereinafter) of RF tag 16 in contact with or in space relation with absorbent material 14. One or more other RF tags 16' can also be positioned between outer cover 10 and inner lining 12 at a different locations in diaper 2. When two or more RF tags 16, 16' are provided, each RF tag 16, 16' has a uniquely detectable response to a wireless excitation signal.

Inner lining 12 can be fluid permeable or can include a fluid permeable part 18 arranged so that when diaper 2 is worn by a patient, fluid permeable part 18 is positioned to receive fluid discharged from the urine discharge orifice and/or the fecal discharge orifice of the patient.

With reference to FIGS. 2a and 2b, disposable pad 4 can be an incontinence pad, a gauze or pad configured for application to bleeding or oozing wounds of a patient or the sterile pad of a bandage. Disposable pad 4 includes liquid absorbent material 20 received in a casing 22 having a fluid impermeable side 24 and a fluid permeable side 26. RF tag 16 is received in casing 22 in contact with or in spaced relation with absorbent material 20. In use, pad 4 is positioned with fluid permeable side 26 positioned to receive fluid discharged from the patient.

Embodiments of RF tag 16 suitable for use in remote incontinence monitoring and/or remote position monitoring are found in the art of electronic article surveillance (EAS). A nonlimiting example of a first embodiment RF tag 16 and method of use thereof are disclosed in U.S. Pat. Nos. 3,810,147 and 3,967,161 which are incorporated herein by reference.

Figure 4B:
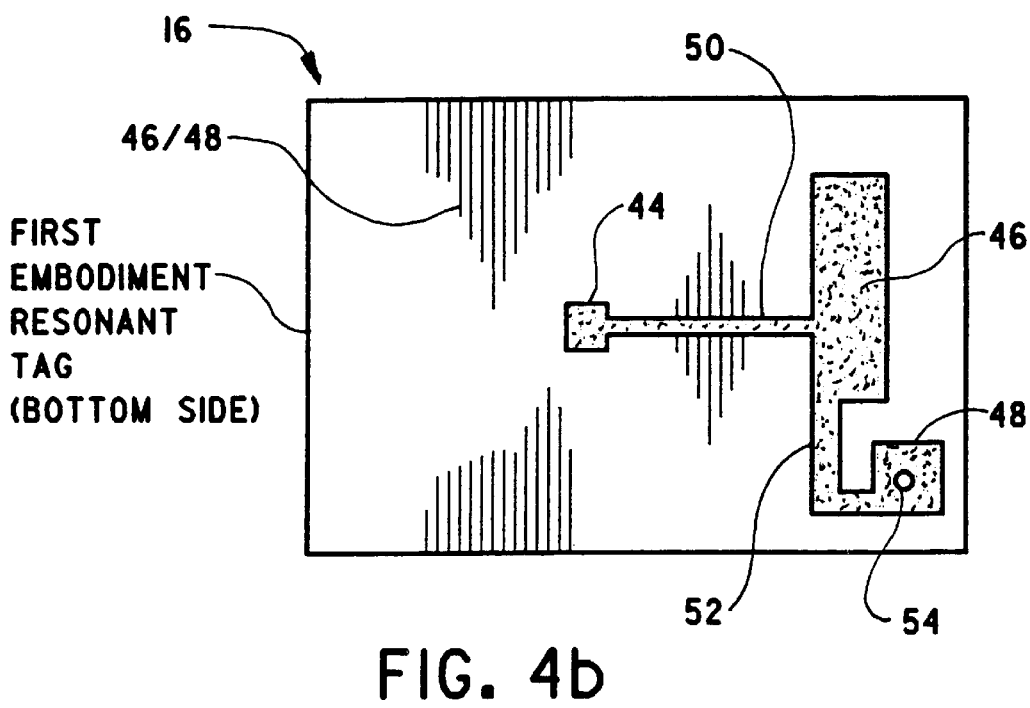

With reference to FIGS. 4a and 4b, one exemplary instantiation of the first embodiment RF tag 16 includes a first conductive path 30 arranged in a generally rectangular pattern on a top surface of a flexible insulating substrate 32 and terminating at one end in a conductive area 34 disposed in spaced relation near one edge of substrate 32. The other end of path 30 terminates at a conductive area 36 disposed near one corner of substrate 32. A second conductive path 38 is formed as a rectangular spiral on substrate 32 and terminates at its outer end at a junction 40 with area 34, and at its inner end at a conductive area 42 centrally of the spiral.

The bottom surface of substrate 32 includes a conductive area 44 in alignment and generally coextensive with conductive area 42. A pair of conductive areas 46 and 48 are positioned in alignment and generally coextensive with areas 34 and 36. Conductive areas 44 and 46 are interconnected by a conductive path 50, while conductive areas 46 and 48 are interconnected by a conductive path 52. An electrical connection 54 is made between areas 36 and 48 by means of a conductive pin or the like extending through substrate 32.

Figure 5:
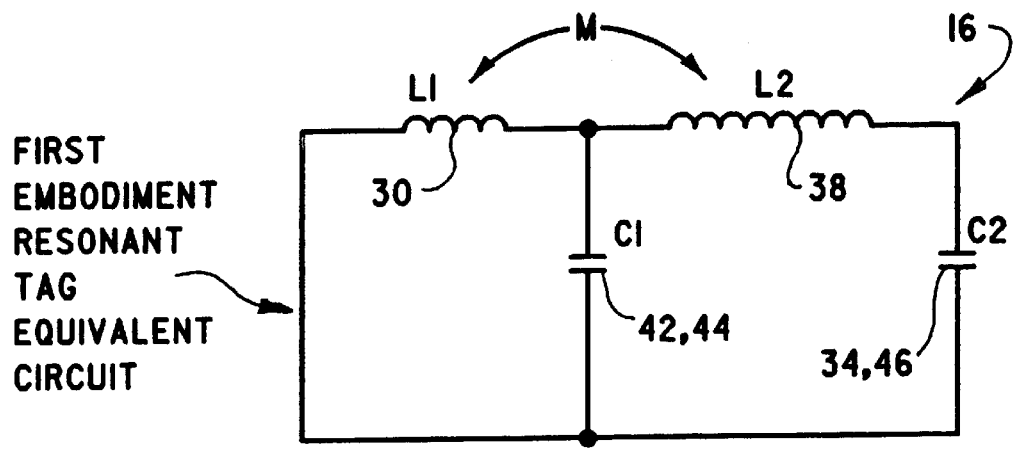
FIG. 5 is an equivalent electrical circuit diagram of the RF tag shown in FIGS. 4a and 4b.

With reference to FIG. 5 and with continuing reference to FIGS. 4a and 4b, conductive paths 30 and 38 define inductors L1 and L2 which act as an antenna of RF tag 16. Conductive areas 42 and 44 spaced by substrate 32 define a first capacitor C1, while conductive areas 34 and 46 spaced by substrate 32 define a second capacitor C2. While the first embodiment RF tag 16 includes two inductors L1 and L2 and two capacitors C1 and C2, this first embodiment RF tag 16 can be modified so that it only includes one inductor L and one capacitor C. The first embodiment RF tag 16 shown in FIGS. 4a and 4b is strictly for the propose of illustration and is not to be construed as limiting the invention.

The first embodiment RF tag 16 can be utilized with remote excitation and detection circuitry in essentially two modes of operation. Namely, an energy absorption mode and an energy radiation mode. Use of the first embodiment RF tag 16 in the energy absorption mode will now be described with reference to FIGS. 6–9.

Figure 6:
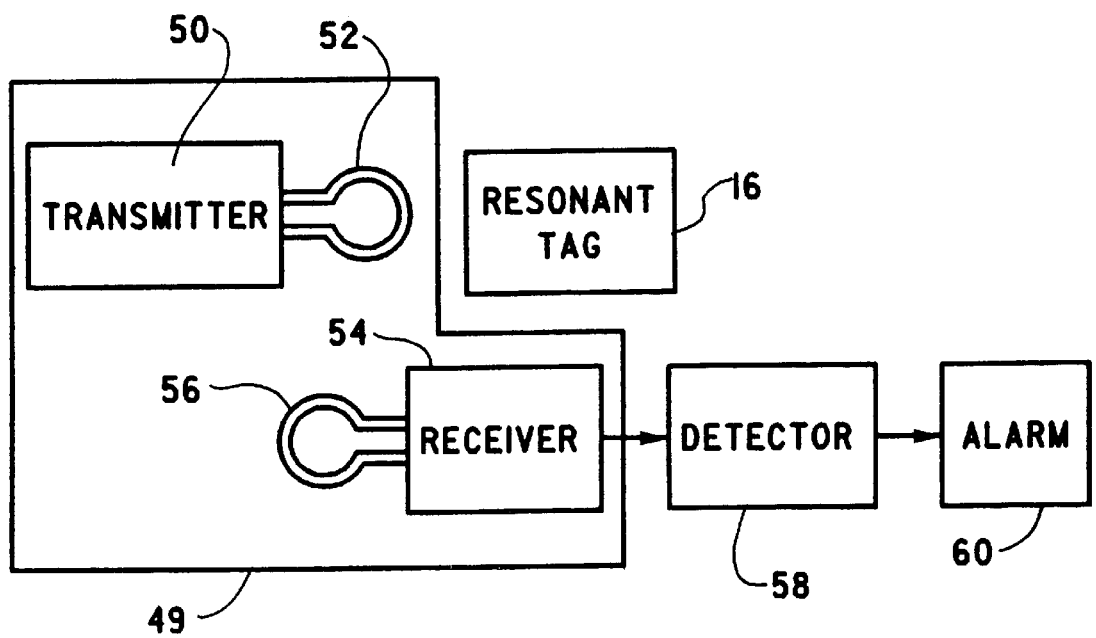
FIGS. 6–10 are schematic drawings of different embodiments of circuits that can be utilized for exciting the first embodiment RF tag shown in FIGS. 4a and 4b with an excitation signal and for detecting the response of the RF tag to the excitation signal.

With reference to FIG. 6, a first circuit for use with the first embodiment RF tag 16 in the energy absorption mode includes a first transceiver 49 for exciting RF tag 16 with a wireless excitation signal and for detecting the response of RF tag 16 to the excitation signal. Transceiver 49 includes a transmitter 50 coupled to an antenna 52 for exciting RF tag 16 with the wireless excitation signal and a receiver 54 coupled to an antenna 56 for wirelessly detecting the response of RF tag 16 to the excitation signal.

In the absence of RF tag 16 in the area between antennas 52 and 56, the excitation signal provided by antenna 52 is sensed by antenna 56 without interference from RF tag 16. However, when RF tag 16 is present between antennas 52 and 56, RF tag 16 couples to the excitation signal provided by antenna 52 when the frequency of the excitation signal is the same as the resonant frequency of RF tag 16. In response to RF tag 16 absorbing energy from the excitation signal, antenna 56 detects a reduction in the signal strength of the excitation signal at the resonant frequency of RF tag 16. In EAS applications, this reduction in the signal strength can be sensed by a detector 58 which is programmed to activate an alarm 60 in response.

Figure 7:
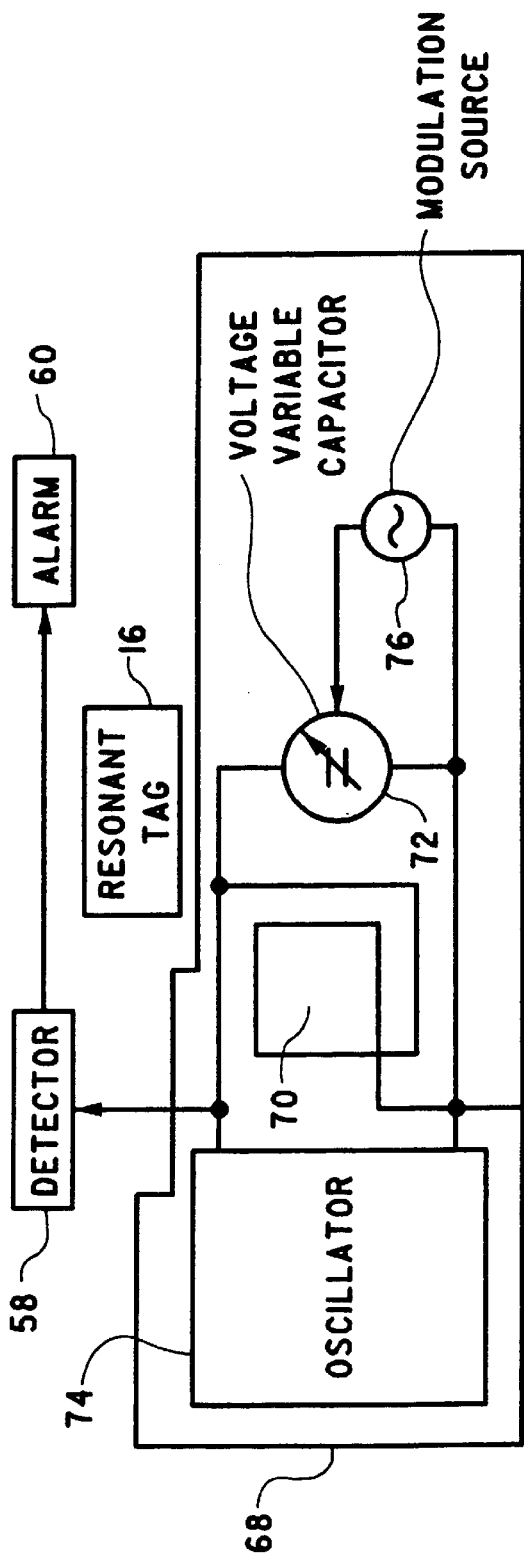

With reference to FIG. 7, a second circuit for use with the first embodiment RF tag 16 in the energy absorption mode includes a transceiver 68 having an antenna loop 70 resonant with a voltage variable capacitor 72 which is driven by an oscillator 74. A modulating signal is provided by a modulation source 76 coupled to a control input of capacitor 72 to vary the capacitance thereof and thus the resonance of the tuned circuit. In operation, when RF tag 16 is coupled with antenna 70, the antenna loop 70 becomes loaded with the reflected impedance of RF tag 16 which produces a change in the voltage across the antenna loop 70. This change can be sensed by detector 58 which activates alarm 60 in response.

Figure 8:
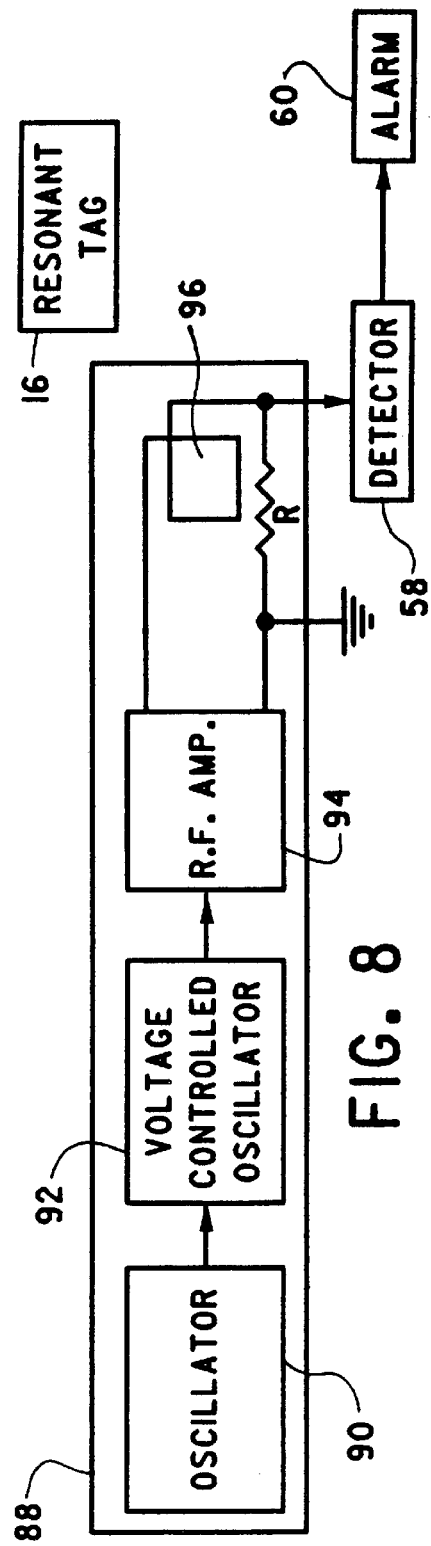

With reference to FIG. 8, a third circuit for use with the first embodiment RF tag 16 in the energy absorption mode includes a transceiver 88 which includes an oscillator 90 which drives a voltage controlled oscillator 92 which, in turn, drives an RF amplifier 94 which energizes a non-resonant loop antenna 96. When RF tag 16 is coupled to antenna 96, the impedance of RF tag 16 is reflected into antenna 96 thereby causing a change in the apparent resistance of antenna 96. This change can be sensed across a resistor R by detector 58 which activates alarm 60 in response.

Figure 9:
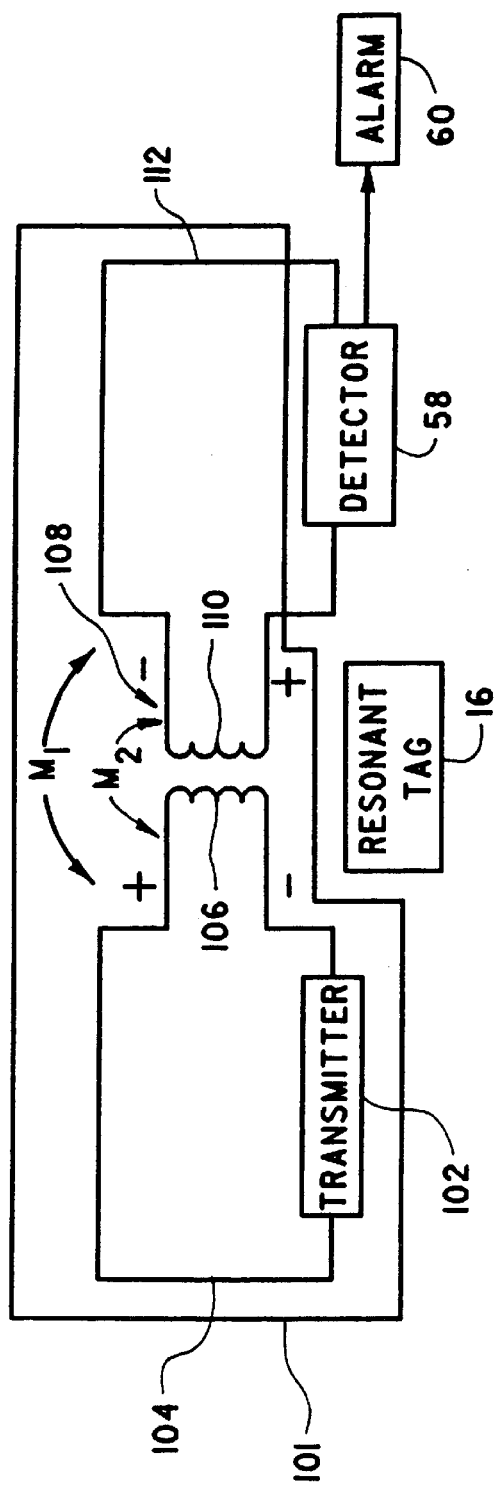

With reference to FIG. 9, a fourth circuit for use with the first embodiment RF tag 16 in the energy absorption mode includes a transceiver 101 having a transmitter 102 coupled to an antenna loop 104 in series with one winding 106 of a transformer 108. Transformer 108 includes another winding 110 in series with an antenna loop 112 of a receiving antenna to which detector 58 is coupled. Transformer 108 has variable mutual coupling $M_2$ that it is adjusted in response to RF tag 16 moving into mutually coupling relationship with antenna loops 104 and 112. In response to a change in the mutual coupling, detector 58 detects a corresponding change in a current flowing in antenna loop 112. This change can be sensed by detector 58 which activates alarm 60 in response.

Next, the use of the first embodiment RF tag 16 in the energy radiation mode will be described with reference to FIGS. 10 and 6.

Figure 10:
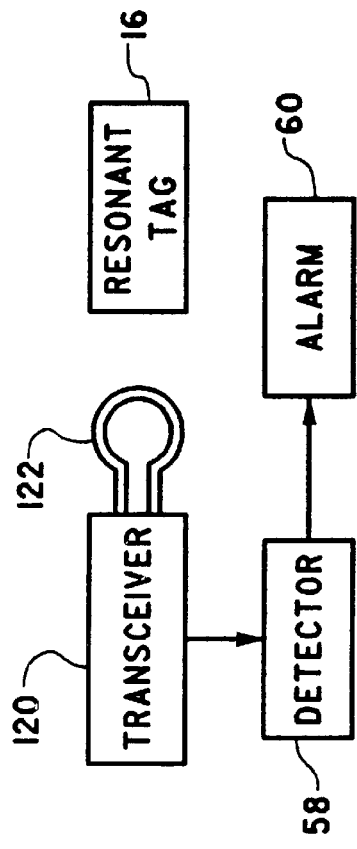

With reference to FIG. 10, a circuit for use with the first embodiment RF tag 16 in the energy radiation mode includes a transceiver 120 which outputs an excitation signal via an antenna 122. In response to RF tag 16 receiving this excitation signal RF tag 16 commences oscillating at its resonant frequency. At a suitable time, transceiver 120 terminates the excitation signal whereupon energy stored in RF tag 16 causes RF tag 16 to continue oscillating at its resonant frequency, thereby generating a wireless response signal, for a brief interval after termination of the excitation signal. During this brief interval, transceiver 120 detects the wireless response signal output by RF tag 16 via antenna 122. In response to detecting the wireless response signal, detector 58 activates alarm 60.

As an alternative to utilizing transceiver 120 to detect the wireless response signal, transceiver 49, shown in FIG. 6, having transmitter 50 and receiver 54 coupled to antennas 52 and 56, respectively, can be utilized to output the excitation signal and receive the wireless response signal output by RF tag 16.

The detection of a wireless response signal output by an RF tag 16 after termination of an excitation signal utilized to excite the RF tag 16 to resonance is disclosed in United States Patent Application Publication No. 2001/0040507 to Eckstein et al.

With reference to FIGS. 11a and 11b, a second embodiment RF tag 16 utilized in an energy radiation mode of operation includes a housing 130 which supports a magnetostrictive element 132 in the magnetic field of a magnet 134. More specifically, magnetostrictive element 132 is suspended in a cavity 136 of housing 130 in a manner whereupon magnetostrictive element 132 is biased by the magnetic field of magnet 134. Also received in cavity 136 is a liquid absorbent material 138. In the absence of discharged fluid, liquid absorbent material 138 is spaced from magnetostrictive element 132.

Figure 12:
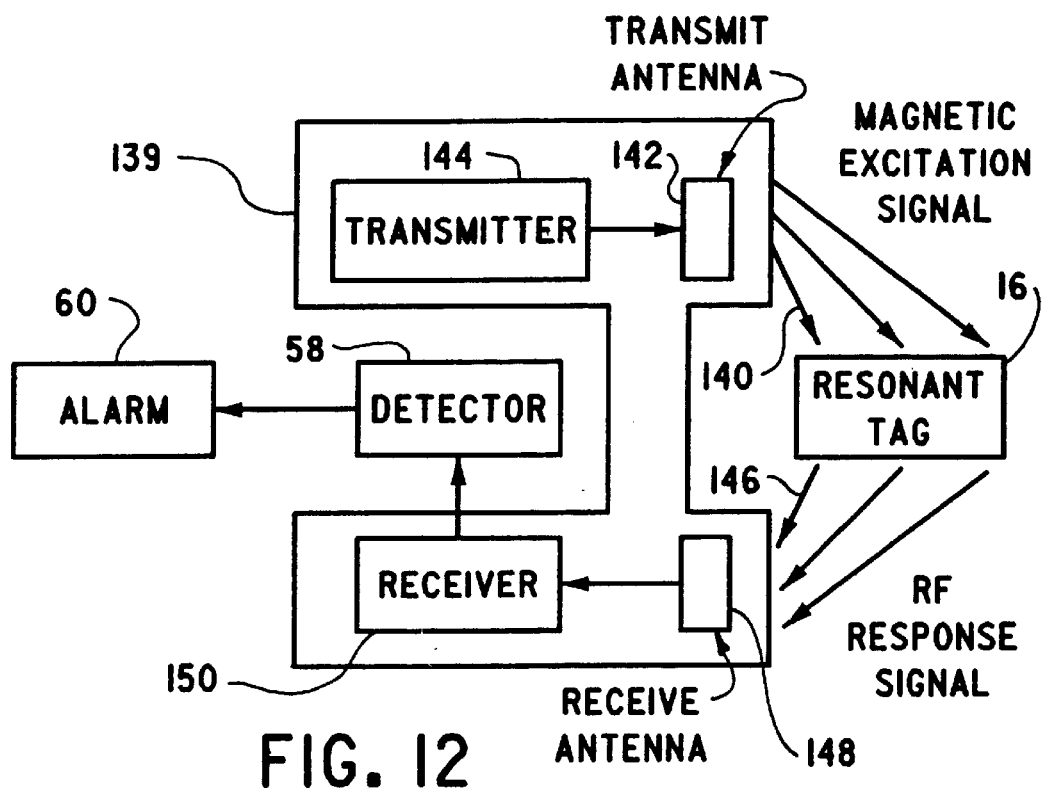
FIG. 12 is a schematic drawing of a circuit for exciting the second embodiment RF tag shown in FIGS. 11a and 11b with an excitation signal and for detecting the response of the RF tag to the excitation signal.

With reference to FIG. 12 and with continuing reference to FIGS. 11a and 11b, a circuit for use with the second embodiment RF tag 16 includes a transceiver 139 for exciting RF tag 16 with an excitation signal and for detecting the response of RF tag 16 to the excitation signal. More specifically, transceiver 139 includes a transmitter 144 that outputs a magnetic excitation signal 140 via a transmit antenna 142. In response to receiving magnetic excitation signal 140, magnetostrictive element 132 commences oscillating at its resonant frequency thereby generating an RF response signal 146 which is received by a receive antenna 148 and processed by a receiver 150. When exposed to discharged fluid, however, liquid absorbent material 138 expands into contact with magnetostrictive element 132, as shown by dashed line 156 in FIG. 11b. This contact inhibits the vibration of magnetostrictive element 132 in response to magnetic excitation signal 140 whereupon the amplitude and/or the frequency of RF response signal 146 changes.

To facilitate the absorption of discharged fluid by liquid absorbent material 138, housing 130 includes one or more apertures 158 which enable discharged fluid to enter cavity 76 whereupon it is absorbed by liquid absorbent material 138. Alternatively, apertures 158 can be omitted and a wicking element (not shown) can be connected between the outside of housing 130 and liquid absorbent material 138 for wicking discharged fluid into liquid absorbent material 138. Still further, apertures 158 and liquid absorbent material 138 can be omitted and all or part of housing 130 can be made of material that swells or weakens and collapses in the presence of discharged fluid, thereby mechanically damping the response of magnetostrictive element 132 to magnetic excitation signal 140. In response to detecting a change in the amplitude and/or frequency of RF response signal 146, detector 58 activates alarm 60.

The second embodiment RF tag 16 shown in FIGS. 11a and 11b is strictly for the purpose of illustration and is not to be construed as limiting the invention. An nonlimiting example of the second embodiment RF tag 16 is disclosed in U.S. Pat. No. 6,182,352 to Deschenes et al.

Figure 13:
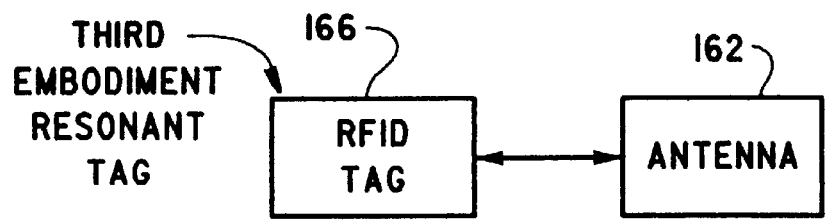
FIG. 13 is a schematic drawing of a third embodiment RF tag which can be excited with an excitation signal output by one of the circuits shown in FIGS. 6–10 and the response of which can be detected thereby.

With reference to FIG. 13, a third embodiment RF tag 16 includes an antenna 162 coupled to a radio frequency identification (RFID) tag 166. RFID tag 166 can be any one of the RFID tags of the type know in the art of EAS that operate in the energy absorption mode or the energy radiation mode. Each prior art RFID tag that operates in the energy absorption mode absorbs energy from the excitation signal used to stimulate the RFID tag in one or more unique frequencies or unique bands of frequencies that can be detected by detector 58. Each prior art RFID tag that operates in the energy radiation mode outputs a unique wireless response signal in response to receiving the excitation signal. Each unique wireless response signal can include, without limitation, one or more frequencies or band of frequencies that can be detected by detector 58. Each wireless response signal output by a prior art energy radiation mode RFID tag may comprise one or more frequencies included in the excitation signal, one or more frequencies not included in the excitation signal or some combination thereof.

The third embodiment RF tag 16 shown in FIG. 13 is strictly for the purpose of illustration and is not to be constructed as limiting the invention. One, nonlimiting example of a third embodiment RF tag 16 is disclosed in U.S. Pat. No. 5,963,134 to Bowers et al.

The foregoing description of the general operation of the various embodiments of RF tag 16 are included herein for the purpose of illustration and are not to be construed as limiting the invention. To this end, the excitation signal used to stimulate each of the foregoing embodiments of RF tags 16 can be one that is swept from a starting frequency to an ending frequency, a broadband excitation signal or a narrowband excitation signal depending on, among other things, the stimulation requirement of the specific embodiment RF tag 16 being utilized and/or the configuration of the remote excitation and detection circuitry utilized therewith. Hence, the foregoing descriptions of excitation signals used to stimulate the various embodiments of RF tags 16 are strictly for the purpose of illustration and are not to be construed as limiting the invention. Moreover, the circuitry shown in FIGS. 6–10 and 12 are strictly for the purpose of illustration and are not to be construed as limiting the invention.

With reference back to FIGS. 1a, 1b, 2a, 2b, 4a and 4b, use of the various embodiments of RF tag 16 in accordance with the present invention will now be described. In use, diaper 2 or pad 4 is positioned to receive fluid discharged from a patient. In the absence of fluid discharged from the patient, absorbent material 14 or 20 is dry. Under this circumstance, when the first embodiment RF tag 16 operating in the energy absorption mode receives the excitation signal, it selectively absorbs energy from the excitation signal at its resonant frequency. This absorption produces in the excitation signal a unique change that can be detected by detector 58.

However, when the patient discharges fluid into diaper 2 or pad 4, the discharged fluid is absorbed by liquid absorbent material 14 or 20. When the discharged fluid absorbed by liquid absorbent material 14 or 20 contacts inductor L1 or L2 or capacitor C1 or C2, electrolytes contained in this discharged fluid create low resistance paths which detune the first embodiment RF tag 16 thereby changing its resonant frequency. In response to this change, the frequency where energy in the excitation signal is absorbed by the first embodiment RF tag 16 changes. In response to detecting this change in the frequency where energy is absorbed in the excitation signal, detector 58 activates alarm 60.

Since electrolytes contained in the discharged fluid render the discharged fluid conductive, discharged fluid covering all or part of one or both surfaces of RF tag 16 also acts as a shield that attenuates or blocks receipt of excitation signal by inductor L1 or L2 or capacitor C1 or C2. Hence, detector 58 can also or alternatively be configured to detect a change, i.e., a reduction, in the absorption of energy by the first embodiment RF tag 16 due to discharged fluid covering all or part of on one or both surfaces thereof. If sufficient discharged fluid covers one or both surfaces of the first embodiment RF tag 16, the absorption of the excitation signal detected by detector 58 can decrease to zero or null.

To avoid the possibility that discharged fluid may not contain sufficient electrolytes to detune first embodiment RF tag 16 or shield circuit elements L1, L2, C1 or C2 from the excitation signal, a dry or powdered electrolyte, such as salt, can be embedded in absorbent material 14 or 20 or in a wetable membrane 46 covering one or both surfaces of the first embodiment RF tag 16. When discharged fluid contacts this dry or powdered electrolyte, the dry or powdered electrolyte dissolves forming a concentrated electrolyte solution that modifies the resonant frequency of first embodiment RF tag 16 and/or shields circuit elements L1, L2, C1 and/or C2 from the excitation signal.

The use of wetable membrane 46 on one or both surfaces of the first embodiment RF tag 16 engenders detuning and/or shielding of circuit elements L1, L2, C1 and/or C2 of first embodiment RF tag 16 when discharged fluid is present. However, wetable membrane 46 can be replaced by a fluid impermeable coating 48 on one or both surfaces of the first embodiment RF tag 16 for maintaining one or both surfaces in spaced relation to discharged fluid received in absorbent material 14 or 20. The use of coating 48 on one or both surfaces of the first embodiment RF tag 16 engenders shielding circuit elements L1, L2, C1 and/or C2 from receiving the excitation signal.

In the energy radiation mode of operation, where a wireless response signal output by the first embodiment RF tag 16 after termination of the excitation signal is utilized to detect the absence or presence of discharged fluid, detector 58 is configured to detect a change in the resonant frequency of the wireless response signal due to discharged fluid detuning circuit element L1, L2 C1 and/or C2 and/or a change, i.e., a reduction, in the signal strength, e.g., amplitude, of the wireless response signal due to discharged fluid shielding circuit element L1, L2, C1 and/or C2 from the excitation signal. In response to detecting one or both of these changes, detector 58 activates alarm 60.

In accordance with the present invention, the third embodiment RF tag 16 shown in FIG. 13 can be utilized in the energy absorption mode of operation where, in response to receiving an excitation signal in the absence of discharged fluid on or adjacent the third embodiment RF tag 16, RFID tag 166 selectively absorbs energy at one or more unique frequencies and/or bands of frequencies of the excitation signal. However, when discharged fluid is present, it attenuates the excitation signal received by the third embodiment RF tag 16 whereupon the selective absorption by RFID tag 166 of energy at one or more unique frequencies and/or bands of frequencies of the excitation signal is reduced. In response to detecting a suitable reduction in the absorbed energy at one or more frequencies and/or bands of frequencies of the excitation signal, detector 58 activates alarm 60. This reduction in absorbed energy at each of one or more unique frequencies or bands of frequencies of the excitation signal can occur to the point where said absorption is zero or null.

The third embodiment RF tag 16 can also be used in the energy radiation mode of operation where, in response to absorbing energy from the excitation signal via antenna 162 in the absence of discharged fluid on or adjacent the third embodiment RF tag 16, RFID tag 166 outputs via antenna 162 a unique wireless response signal comprised of one or more frequencies or bands of frequencies. However, when discharged fluid is present, it attenuates the excitation signal received by the third embodiment RF tag 16 and/or the unique wireless response signal output by RFID tag 166 whereupon an amplitude of one or more frequencies or bands of frequencies of the unique wireless response signal is reduced. In response to detecting a suitable reduction in the amplitude of one or more frequencies or bands of frequencies of the unique wireless response signal, detector 58 activates alarm 60. This reduction in the amplitude of one or more frequencies or bands of frequencies can occur to the point where said amplitude is zero or null.

With reference back to FIGS. 11a, 11b and 12, in accordance with the present invention, the second embodiment RF tag 16 is utilized exclusively in the energy radiation mode of operation. In this mode of operation, when detector 58 detects a change in the amplitude or frequency of RF response signal 146 due to the presence of discharged fluid, detector 58 activates alarm 60. Absent a change in the amplitude or frequency of RF response signal 146, detector 152 takes no action.

As discussed above, the various embodiments of RF tag 16 can be utilized to detect the absence and presence of discharged fluid. To avoid premature or early detection of the presence of discharged fluid when diaper 2 or pad 4 does not need to be changed immediately, one of the various embodiments of RF tag 16 can be positioned at a suitable location in diaper 2 or pad 4 so that liquid absorbent material 14 and 20 absorbs a minimum volume of discharged fluid before the actual or detected operation of RF tag 16 is affected. Moreover, as shown in FIG. 1, diaper 2 can include two or more RF tags 16 and 16', each having a different unique response to an excitation signal, positioned at different locations in diaper 2. These two or more RF tags 16, 16' can be utilized to detect the remaining capacity of diaper 2, especially liquid absorbent material 14, to absorb discharged fluid. For example, a plurality of RF tags 16, 16' can be positioned increasingly distant from the discharge orifice(s) of the patient wearing diaper 2. As discharged fluid covers or comes into contact with each RF tag 16, 16', its unique response varies in one of the manners described above. When the first RF tag 16 of the plurality is covered, its unique response changes whereas the unique response of the other RF tags, e.g., 16' is unaffected. This indicates that diaper 2 is partially full.

When the discharged fluid covers or comes into contact with the RF tag, e.g., 16,' furthest away from the discharge orifice(s) of the patient, its unique response changes whereupon it can be determined that diaper 2 is nearing or has reached its capacity to absorb discharged fluid. The changing of the unique response of each of a plurality of RF tags 16, 16' can be utilized as a basis for determining the urgency with which diaper 2 must be changed based on the remaining capacity of diaper 2 to store discharged fluid. In a similar manner, pad 4 can include two or more RF tags 16, 16' for determining when pad 4 is reaching its capacity to store discharged fluid.

It is envisioned that under certain circumstances where the change in energy absorbed by RF tag 16 and/or the change in a response signal output by RF tag 16 is utilized as the basis for determining the presence of discharged fluid, it may be desirable to also provide a means for detecting that the patient is adjacent the transceiver that excites and detects the response of RF tag 16. This is especially desirable for remote detection of the absence or presence of discharged fluid where the transceiver is positioned to detect an RF tag 16 associated with a patient lying on a bed or sitting in a wheelchair. To this end, diaper 2 and/or pad 4 can include a second RF tag 16', having a different unique response than RF tag 16, positioned where it will not be exposed to discharged fluid. Thus, while RF tag 16 can be utilized to detect for the presence or absence of discharged fluid, RF tag 16' is utilized to detect for the presence or absence of the patient adjacent the transceiver. In the case where no response to the excitation signal is received from RF tag 16 and RF tag 16', it is assumed that the patient is not within the range of the transceiver. In contrast, when no response to the excitation signal is received from RF tag 16 but a response is received from RF tag 16', it can be assumed that RF tag 16 is operating in the presence of discharged fluid.

Two RF tags 16 can be located in diaper 2 to emphasize the detection of urine discharge and moist fecal discharge. To this end, diaper 2 can be configured whereupon absorbent material 14 causes discharged urine to move laterally away from its entry point into diaper 2. Accordingly, to avoid premature detection of the presence of discharged fluid, one RF tag 16 can be positioned at a location in diaper 2 to delay the detection of discharged urine. In contrast, it is desired that a second RF tag 16 be located in diaper 2 to quickly detect for the presence of moist fecal discharge.

More specifically, two or more RF tags 16 can be located in diaper 2 to differentially detect if it is dry, if just urine is present, and/or if moist fecal discharge is present. Modern diapers are arranged to quickly wick urine away from the skin surrounding the body's urine discharge orifice and to stabilize it in deep layers of the diaper. However, fecal discharge is trapped next to the patient's skin. When wet with urine, fecal enzymes may be re-activated to irritate or even digest adjacent skin. Therefore, not all wet diapers need to be immediately changed since, depending on the quantity of urine discharged, they can be constructed to contain several urine discharges before reaching their fluid holding capacity. In contrast, it is almost always important to rapidly change a diaper soiled with fecal discharge.

Accordingly, one or more uniquely identifiable RF tags 16 can be located within deep moisture retaining structures of diaper 2 for detecting the presence of discharged fluid and/or when diaper 2 is reaching its fluid retaining capacity. Still further, one or more other uniquely identifiable RF tags 16, especially those coated with a dry electrolyte containing wetable membrane 46, can be located in diaper 2 adjacent the patient's fecal discharge orifice for detecting the presence of fecal discharge. Preferential response to fecal discharge can be enhanced by placing a moisture resistant barrier under the RF tag 16 near the patient's fecal discharge orifice to avoid discharged urine received in diaper 2 from affecting its response. This moisture barrier avoids discharged urine from spreading to the RF tag 16 near the fecal discharge orifice thereby making it more likely that this RF tag 16 will respond to moist fecal discharge.

Detector 58 can be programmed to detect the response of these RF tags 16 to one or more excitation signals and to activate alarm 60 when diaper 2 is full with urine and/or when it is likely that diaper 2 has been soiled with fecal discharge.

Referring back to FIGS. 4a, 4b and 5, to avoid patient discomfort when wearing diaper 2 or lying on pad 4, the first embodiment RF tag 16 preferably comprises flexible substrate 32 that flexes in response to interaction with the patient. In the simplest case where RF tag 16 includes of only one inductor L and one capacitor C, and is resonant at only one frequency, flexing RF tag 16 causes a change in the inductance of inductor L whereupon the resonant frequency of such first embodiment RF tag 16 would change thereby adversely affecting the detection of RF tag 16 which has not yet been exposed to discharged fluid. To avoid this problem, the first embodiment RF tag 16 preferably includes a single circuit having two or more inductors and two or more capacitors, resulting in a circuit having two or more distinct resonant frequencies, with a predetermined frequency difference therebetween, formed on flexible substrate 32. For example, the first embodiment RF tag 16 shown in FIGS. 4a and 4b includes a first inductor circuit element formed by conductive path 30, in parallel with conductive areas 42 and 44, i.e., capacitor C1. Further, the series connected circuit elements L2, formed by conductive path 30, and C2, formed by conductive areas 34 and 46, are themselves additionally connected in parallel with L1 and C1, forming the equivalent circuit shown in FIG. 5. Since inductors L1 and L2 are generally coaxial and coplanar with each other, when the first embodiment RF tag 16 is subject to flexing, the inductances of inductors L1 and L2 change substantially by the same amount whereupon the first resonant frequency, determined substantially by L1, changes by the same amount as the second resonant frequency, determined substantially by L2, and so the frequency difference therebetween remains constant.

Figure 14:
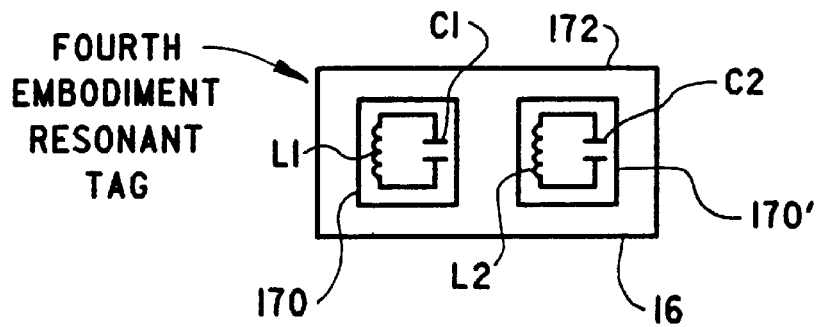
FIG. 14 is a schematic drawing of a fourth embodiment RF tag.

The frequency difference of the first embodiment RF tag 16 can be utilized to identify a particular RF tag 16 in a group of RF tags 16 where each one has a unique frequency difference. In the absence of discharged fluid, the first and second resonant frequencies of the first embodiment RF tags 16 each have a first amplitude in response to an excitation signal. However, when discharged fluid is present in diaper 2 or pad 4, the first and second resonant frequencies of the first embodiment RF tags 16 each have a second, reduced amplitude response to the excitation signal. This difference in amplitude can be utilized in the energy absorption mode of operation and/or in the energy radiation mode of operation for detecting the absence or presence of discharged fluid. Moreover, as shown in FIG. 14, a fourth embodiment RF tag 16 having resonant circuits 170 and 170', each having a different response to an excitation signal, spaced from each other on a flexible insulating substrate 172 can be utilized in place of the first embodiment RF tag 16, albeit with less control of the mutual change in the inductance's of inductors L1 and L2 when substrate 172 is flexed.

As can be seen, the combination of diaper 2 or pad 4, liquid absorbent material 14 or 20 and one or more RF tags 16 enables remote detection of the absence and presence of discharged fluid without having to physically inspect diaper 2 or pad 4. This is particularly useful in hospital and/or nursing home environments where physical inspection may unnecessarily disrupt the patient when diaper 2 or pad 4 does not need to be changed. Moreover, while pad 4 has been described in connection with an incontinence pad, pad 4 can also take the form of a bandage or other type of gauze or pad configured for application to bleeding or oozing wounds of a patient.

In addition to their use in the third embodiment RF tag 16 described above, prior art RFID tags 166 that produce patterns of unique frequencies or bands of frequencies in either the energy absorption mode or energy radiation mode of operation can also be utilized for patient identification. Specifically, some prior art RFID tags can absorb energy from plural, e.g., up to 64, unique frequencies or bands of frequencies of an excitation signal or can output a response signal having plural, e.g., up to 64, unique frequencies or bands of frequencies. In use, these prior art RFID tags are affixed to diapers 2 and/or pads 4. Each patient in a particular location, e.g., a nursing home, is then associated with pattern of frequencies or bands of frequencies produced by RFID tags 166 that is unique from the pattern of frequencies or bands of frequencies associated with other patients. Each patient would then only used diapers 2 or pads 4 having RFID tags 166 including the unique pattern of frequencies or bands of frequencies assigned to that patient. A suitable excitation signal can then be utilized to stimulate one or more third embodiment RF tags 16, each including an RFID tag 166 that produces a pattern of frequencies or bands of frequencies that is unique to a particular patient. From the response to this excitation signal, the location and/or identity of one or more of the patients can be determined.

With reference back to FIGS. 1a, 1b, 3a and 3b, use can be made of two or more RF tags 16 for positioning monitoring of a patient. This use of two or more RF tags 16 is particularly useful for bedridden or wheelchair confined patients for prevention of pressure ulcers, also known as bedsores. In connection with position monitoring, two or more RF tags 16, e.g., RF tags 16A, 16B and 16C can be affixed to underwear 6 or disposable diaper 2. Each RF tag 16A–16C produces a unique response to an excitation signal that can be detected independent of the response of the other RF tags to the excitation signal. RF tags 16A–16C can be affixed on or adjacent a waistband 180 of underwear 6 or waistband 178 of diaper 2, with RF tag 16A positioned adjacent the patient's left hip, RF tag 16B positioned adjacent the patient's right hip and RF tag 16C positioned adjacent the patient's lower back.

Figure 15:
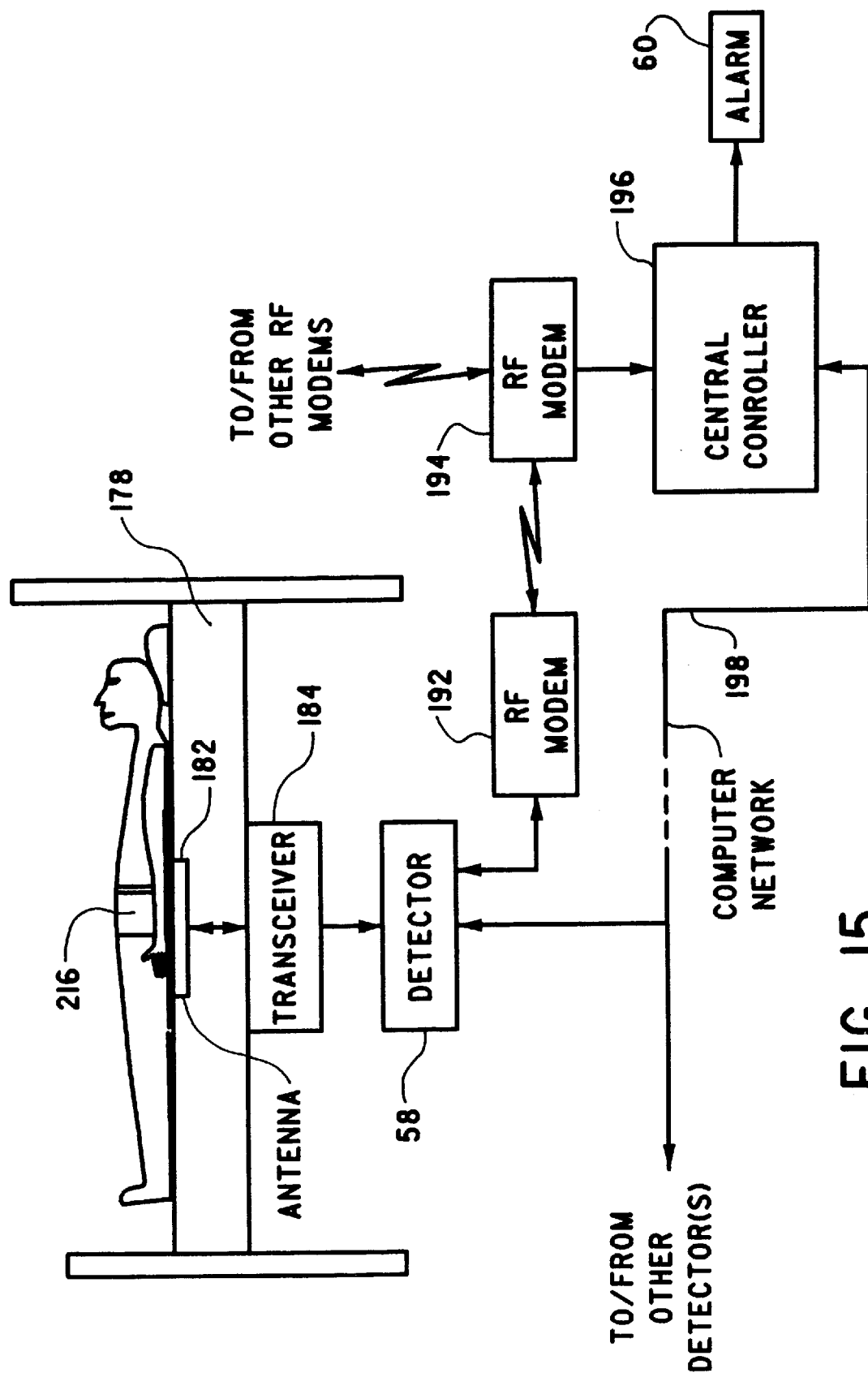
FIG. 15 is a schematic illustration of a supine patient wearing the diaper shown in FIGS. 1a and 1b or the undergarment shown in FIGS. 3a and 3b having a circuit for exciting the RF tags thereof with an excitation signal and for detecting the response of the RF tags to the excitation signal.

With reference to FIG. 15 and with continuing reference to FIGS. 1a, 1b, 3a and 3b, when a patient wearing diaper 2 or underwear 6 having RF tags 16A–16C affixed thereto lies supine on a mattress 178, RF tag 16C will most strongly interact with an antenna 182 which is positioned on or adjacent a surface of mattress 178.

In use, a transceiver 184 excites RF tags 16A–16C with an excitation signal via antenna 182 and detects the unique response of each RF tag 16A–16C to said excitation signal. Detector 58 determines from the detected response of each RF tag 16A–16C, especially the amplitude of the unique energy absorption of the excitation signal caused by each RF tag 16A–16C or from the amplitude of the unique wireless response signal output by each RF tag 16A–16C, which RF tag 16A–16C is closet to antenna 182. For example, when the patient is on his right side, RF tag 16B is closet to the surface of mattress 178 and will return to antenna 182 the strongest response to the excitation signal. Similarly, when the patient is on his left side, RF tag 16A is closet to the surface of mattress 178 and will return to antenna 182 the strongest response to the excitation signal. In general, the strongest response to the excitation signal detected by antenna 182 is received from the RF tag 16A–16C that is closet to antenna 182.

Figure 16:
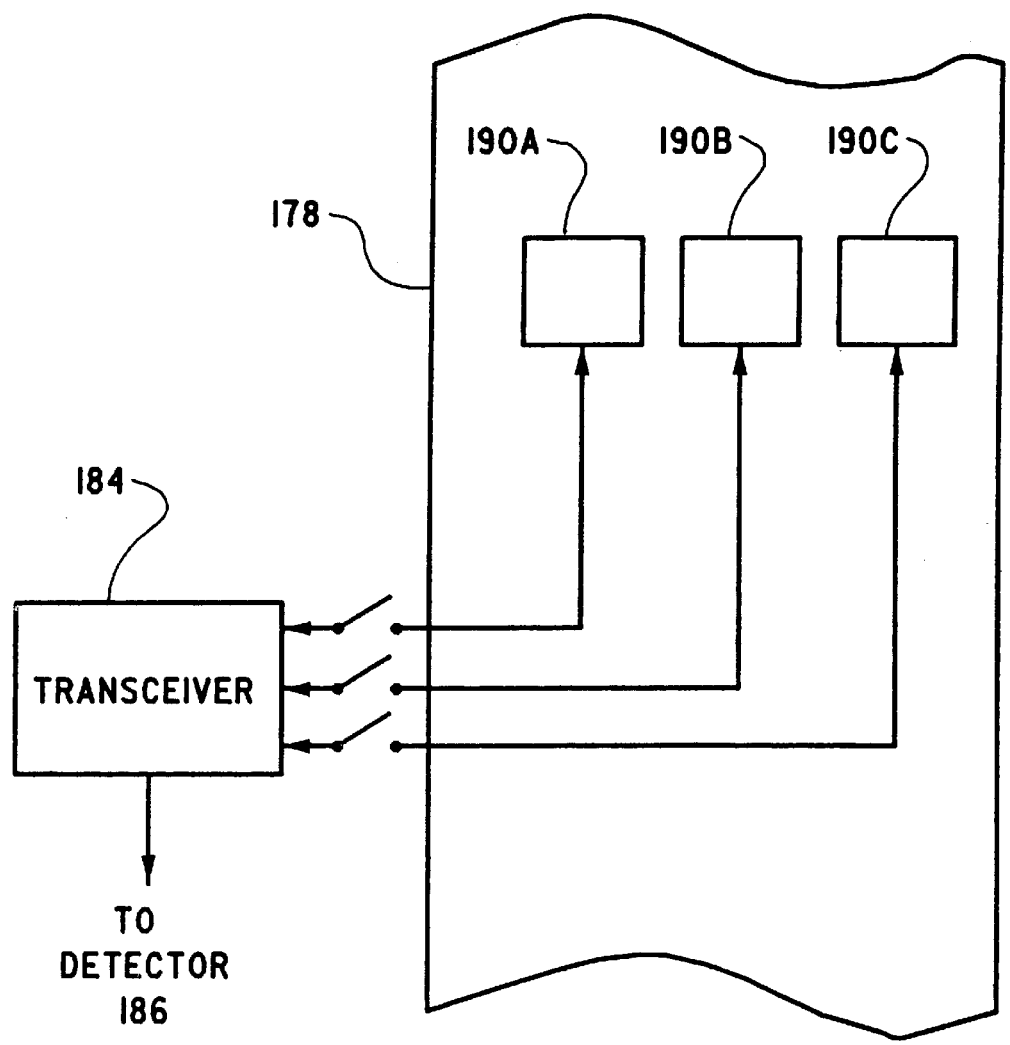
FIG. 16 is an isolated view of the mattress shown in FIG. 15 including a plurality of antennas supported thereby.

With reference to FIG. 16 and with continuing reference to FIG. 15, mattress 178 can include one large antenna 182 or a plurality of small antenna 190A–190C selectively, individually connectable to transceiver 184. In operation, each antenna 190A–190C is selectively connected to transceiver 184 which causes each antenna 190A–190C to output an excitation signal and which detects the response of each RF tag 16A–16C responding to the excitation signal. By determining which antenna 190A–190C has the maximum response, the horizontal location of the patient on mattress 178 can be determined. Moreover, from either the unique energy absorption of the excitation signal caused by each RF tag 16A–16C or from the unique response signal output by each RF tag 16A–16C, the orientation of the patient wearing diaper 2 or underwear 6 can be determined.

When the response of two or more antenna 190A–190C indicate that two RF tags 16A–16C are equally near said antennas, but no RF tag 16A–16C is coupled to the maximum amount possible, it can be concluded that the patient wearing diaper 2 or underwear 6 is oriented between the three positions where an RF tag 16A–16C is parallel to one of antennas 190A–190C. Moreover, if no antenna 190A–190C detects the response of RF tag 16C, but responses are detected from RF tags 16A and 16B, it can be concluded that the patient wearing diaper 2 or underwear 4 is lying prone facedown. This may be considered a dangerous position for a movement impaired patient on a soft mattress 178. Moreover, if no response is detected from RF tag 16A, but sub-maximum responses are detected from RF tag 16B and 16C, it can be concluded that the patient wearing diaper 2 or underwear 6 is oriented about halfway between supine and his right side.

With reference back to FIG. 15, detector 58 can be coupled to an RF modem 192 for wirelessly communicating data regarding the incontinence status of the patient and/or data regarding the position of the patient to a central controller 196 via an RF modem 194 coupled thereto. Other RF modems (not shown) can also communicate like data to central controller 196 via RF modem 194. Alternatively, detector 58 and one or more other detectors (not shown) can be communicatively connected to central controller 196 via a computer network 198. Regardless of the manner in which central controller 196 receives data regarding the incontinence status or position status of a particular patient, central controller 196 can evaluate this data and activate alarm 60 when a diaper 2 or pad 4 of a particular patient needs to be changed and/or when the position of a particular patient requires changing to avoid pressure ulcers.

Detector 58 and/or central controller 196 can be programmed as desired to store for each patient the response of each RF tag 16 to one or more excitation signals. From this data, a change in the incontinence status and/or position of a particular patient can be determined. For example, data regarding the response of each RF tag 16 in one or both of energy absorption mode and/or energy radiation mode of operation, in the absence of discharged fluid can be stored for future comparison with the response of RF tag 16 when discharged fluid is present. Similarly, each change or lack of change in the position of a patient determined from the strength of energy absorption and/or energy radiation from a plurality of RF tags 16 can be stored. This data can then be analyzed by detector 58 and/or center controller 196 in a manner known in the art to determine the absence or presence of discharged fluid and/or whether the patient is changing positions sufficiently often to avoid pressure ulcers.

As can be seen, the present invention enables remote incontinence and position monitoring quickly and efficiently. It enables accurate determination of the need to change a diaper 2 or pad 4 and/or of the need to reposition a patient to avoid pressure ulcers.

The present invention has been described with reference to the preferred embodiments. Obvious modifications and alterations will occur to others upon reading and understanding the preceding detailed description. For example, when used for position monitoring, any article which can be worn or affixed to a patient whereupon the RF tags 16 thereof are positioned on or adjacent known points of the patients anatomy can be utilized. Moreover, one or more of these RF tags 16 can be disposed in diaper 2 or underwear 6 at locations other than waistband 178 or 180. In addition, RF tags 16 included in diaper 2 and/or underwear 6 used for position monitoring can also be used to detect for the presence or absence of discharged fluid. It is intended that the invention be construed as including all such modifications and alterations insofar as the come within the scope of the appended claims or the equivalents thereof.

The invention claimed is:

1. A patient fluid discharge monitoring system comprising:
   a liquid absorbent material configured to be positioned to receive fluid discharged from a patient; and
   a first RF tag having one of (i) an inductor—capacitor resonator formed on a flexible insulating substrate wherein the capacitor includes conductive areas in alignment on opposite sides of the substrate and (ii) an antenna coupled to an RFID tag, the first RF tag positioned in contact with or in spaced relation with the liquid absorbent material, the first RF tag configured to absorb a wireless excitation signal whereupon a change in the amount of discharged fluid received in the liquid absorbent material causes a change in the absorption of the energy of the wireless excitation signal by the first RF tag wherein said latter change is detectable remotely in the absence of detecting energy radiated by the first RF tag.

2. The system as set forth in claim 1, further including a remote transmitter for transmitting the wireless excitation signal and for detecting the change in the absorption of the energy of the wireless excitation signal by the first RF tag.

3. The system as set forth in claim 2, further including an alarm responsive to the change detected by the transmitter.

4. The system as set forth in claim 1, wherein:
   at least one of the liquid absorbent material and the first RF tag includes a dry electrolyte;
   in response to the discharged fluid combining with the dry electrolyte, said combination causes the change in the absorption of the wireless excitation signal; and
   the change in absorption of the energy of the wireless excitation signal includes a change in a frequency of absorption of the energy of the first RF tag.

5. The system as set forth in claim 4, wherein:
   at least one of the liquid absorbent material and the first RF tag includes a dry electrolyte;
   in response to the discharged fluid combining with the dry electrolyte, said combination causes the change in the absorption of the excitation signal; and
   the change in absorption of the energy of the wireless excitation signal includes reducing the absorption of the energy of the wireless excitation signal by the first RF tag at at least one frequency.

6. The system as set forth in claim 1, wherein the absorbent material is received in one of:
   a diaper having the absorbent material and the first RF tag received between an inner lining and an outer cover, where at least part of the inner lining is fluid permeable; and
   a pad having the absorbent material and the first RF tag received in a casing, where at least part of the casing is fluid permeable.

7. The system as set forth in claim 6, wherein the pad is one of an incontinence pad, a gauze or pad configured for application to bleeding or oozing wounds of a patient or a sterile pad of a bandage.

8. The system as set forth in claim 1, further including a second RF tag having one of (i) an inductor—capacitor resonator formed on a flexible insulating substrate wherein the capacitor includes conductive areas in alignment on opposite sides of the substrate and (ii) an antenna coupled to an RFID tag, the second RF tag positioned in contact with or in spaced relation with the liquid absorbent material, the second RF tag configured to absorb a wireless excitation signal whereupon a change in the amount of discharged fluid received in the liquid absorbent material causes a change in the absorption of the energy of the wireless excitation signal by the second RF tag wherein said latter change is detectable remotely in the absence of detecting energy radiated by the second RF tag.

9. The system as set forth in claim 8, wherein the second RF tag is spaced from the first RF tag whereupon discharged fluid received in the absorbent material first causes the first RF tag to respond and change its absorption of the energy of the wireless excitation signal and then causes the second RF tag to respond and change its absorption of the energy of the wireless excitation signal.

10. The system as set forth in claim 1, wherein:
at least one of the liquid absorbent material and the RF tag includes a dry electrolyte; and
in response to the discharged fluid combining with the dry electrolyte, said combination shields the RF tag from the excitation signal whereupon the RF tag is not exposed to the wireless excitation signal.

11. A patient fluid discharge monitoring system comprising:
a liquid absorbent material configured to be positioned to receive fluid discharged from at least one of a urine discharge orifice and a fecal discharge orifice of a patient; and
a first RF tag positioned in contact with or in spaced relation with the liquid absorbent material, the first RF tag responsive to a wireless excitation signal in the absence of discharged fluid in the liquid absorbent material and responsive to the excitation signal in the presence of discharged fluid in the liquid absorbent material for causing at least one of (i) a unique change in the excitation signal and (ii) a change in a unique wireless response signal output by the first RF tag in response to the wireless excitation signal, wherein:
the first RF tag is formed on a flexible substrate;
the first RF tag includes two circuits, with each circuit responsive to the liquid absorbent material receiving discharged fluid for causing at least one of (i) the unique change in the excitation signal and (ii) the unique change in the wireless response signal output by the first RF tag in response to the excitation signal, the two circuits having a difference in the unique changes in the excitation signal caused thereby or a difference in the unique changes in the wireless response signal caused thereby; and
flexing of the substrate alters together the unique changes in the excitation signal or the unique changes in the wireless response signal caused by the circuits whereby the difference therebetween remains substantially the same.

12. A patient fluid discharge monitoring system comprising:

an article configured to be positioned adjacent a patient, the article including an absorbent material for absorbing fluid discharged by the patient;
an RF tag positioned adjacent the absorbent material, the RF tag having one of (i) an inductor—capacitor resonator formed on a flexible insulating substrate wherein the capacitor includes conductive areas in alignment on opposite sides of the substrate and (ii) an antenna coupled to an RFID tag, the RF tag operative for absorbing a wireless excitation signal; and
a dry electrolyte adjacent at least part of the RF tag, wherein the the dry electrolyte and the RF tag are arranged whereupon in the absence of discharged fluid in the absorbent material, the RF tag exhibits a first characteristic absorption of the energy of the wireless excitation signal that is detectable remotely in the absence of detecting energy radiated by the RF tag and in the presence of discharged fluid combined with the dry electrolyte in the absorbent material, the RF tag exhibits a second characteristic absorption of the energy of the wireless excitation signal that is detectable remotely in the absence detecting energy radiated by the RF tag.

13. The system as set forth in claim 12, wherein the second characteristic absorption of the energy of the wireless excitation signal is a null.

14. The system as set forth in claim 12, further including a transmitter for generating the wireless excitation signal, for detecting a change between the first and second characteristic absorption's of the energy of the energy wireless excitation signal, and for generating a signal as a function of said change.

15. The system as set forth in claim 12, wherein a change in the first and the second characteristic absorption's of the energy of the wireless excitation signal includes a change in at least one frequency where the energy of the wireless excitation signal is absorbed.

16. The system as set forth in claim 12, wherein a change in the first and the second characteristic absorption's of the energy of the wireless excitation signal includes a change in the amount of energy of the wireless excitation signal that is absorbed at at least one frequency.

17. A patient fluid discharge monitoring system comprising:
an article configured to be worn next to the skin of a patient, the article including an absorbent material for absorbing fluid discharged by the patient; and
an RF tag positioned adjacent the absorbent material, wherein the absorbent material and the RF tag are arranged whereupon in the absence of fluid in the absorbent material, the RF tag is responsive to a wireless excitation signal and in the presence of fluid in the absorbent material, the response of the RF tag to the excitation signal changes, wherein:
the RF tag is positioned in the article to provide a first delay between the first and second detected responses thereof when the article initially receives discharged fluid in the form of urine; and
the system further includes another RF tag positioned in the article to provide a second delay between the first and second detected responses thereof when the article initially receives discharged fluid in the form of moist fecal discharge.

18. The system as set forth in claim 17, wherein the article includes a moisture barrier arranged adjacent the other RF tag for avoiding discharged urine from causing the change from its first detected response to its second detected response.

19. A method of monitoring patient fluid discharge comprising the steps of:

(a) providing at least one article configured to be worn by a patient, the article having absorbent material and an RF tag adjacent the absorbent material, the RF tag having one of (1) an inductor—capacitor resonator formed on a flexible insulating substrate wherein the capacitor includes conductive areas in alignment on opposite sides of the substrate and (2) an antenna coupled to an RFID tag;

(b) exciting the RF tag with an excitation signal;

(c) wirelessly detecting an absorption of energy of the excitation signal by the RF tag at at least one frequency in the absence of detecting energy radiated by the RF tag when patient discharged fluid is present in the absorbent material; and (d) determining from the detected absorption of the energy of the excitation signal at the at least one frequency that patient discharged fluid is present in the absorbent material.

20. The method as set forth in claim 19, wherein the detected absorption of the excitation signal is a null.

21. The method as set forth in claim 19, further including generating an alarm in response to step (d).

22. The method as set forth in claim 19, wherein:

at least one of the absorbent material and the RF tag includes a dry electrolyte; and in response to the discharged fluid combining with the dry electrolyte, the detected absorption of the energy of the excitation signal by the RF tag at the at least one frequency decreases.

23. The method as set forth in claim 19, wherein:

at least one of the absorbent material and the first RF tag includes a dry electrolyte; and in response to the discharged fluid combining with the dry electrolyte, the at least one frequency of absorption of the energy of the excitation signal by the RF tag changes.

24. A patient fluid discharge monitoring system comprising:

a diaper having absorbent material received between a fluid impermeable cover and a fluid permeable lining;

a plurality of first RF tags each uniquely identifiable and each positioned near or adjacent at least one of the fluid impermeable cover and the absorbent material adjacent the fluid impermeable cover, the plurality of first RF tags distributed throughout the diaper and responsive to a wireless excitation signal for providing an indication of how much capacity of the absorbent material is available for receiving urine; and at least one uniquely identifiable second RF tag positioned in the diaper near or adjacent the fluid permeable lining or in the absorbent material adjacent the fluid permeable lining in an area of the diaper configured to be positioned adjacent an anus of a patient when worn, the at least one second RF tag responsive to the wireless excitation signal for providing an indication of the absence and presence of feces near or adjacent the at least one second RF tag.

25. The system as set forth in claim 24, further including a moisture resistant barrier positioned in the diaper to avoid urine received in the absorbent material from contacting each second RF tag.

26. A patient fluid discharge monitoring system comprising:

a first liquid absorbent material configured to be positioned to receive fluid discharged from a patient; and an RF tag having a magnetostrictive element biased in a magnetic field of a magnet, the RF tag positioned in contact with or in spaced relation with the first liquid absorbent material, wherein:

in response to receiving a wireless excitation signal in the absence of the discharged fluid in the liquid absorbent material, the RF tag re-radiates energy received from the wireless excitation signal as a first RF response signal; and in response to receiving a wireless excitation signal in the presence of the discharged fluid in the liquid absorbent material, the RF tag re-radiates energy received from the wireless excitation signal as a second RF response signal.

27. The system as set forth in claim 26, wherein the second RF response signal is a null.

28. The system as set forth in claim 26, wherein:

the magnetostrictive element vibrates to produce the first RF response signal; and the vibration of the magnetostrictive element is suppressed to produce the second RF response signal.

29. The system as set forth in claim 26, wherein:

the RF tag includes a second liquid absorbent material that expands into contact with the magnetostrictive element when the second liquid absorbent material is exposed to the discharged fluid; and said contact suppresses vibration of the magnetostrictive element; and the second RF response signal is the suppressed vibration of the magnetostrictive element in response to receiving the wireless excitation signal.

* * * * *

UNITED STATES PATENT AND TRADEMARK OFFICE
CERTIFICATE OF CORRECTION

PATENT NO. : 6,774,800 B2
DATED : August 10, 2004
INVENTOR(S) : Friedman et al.

It is certified that error appears in the above-identified patent and that said Letters Patent is hereby corrected as shown below:

Column 16,
Line 48, "as set forth in claim 4" should read -- as set forth in claim 1 --

Signed and Sealed this

Twenty-second Day of February, 2005

JON W. DUDAS
*Director of the United States Patent and Trademark Office*